United States Patent [19]

Zacharias

[11] Patent Number: 5,720,742
[45] Date of Patent: Feb. 24, 1998

[54] CONTROLLER AND ACTUATING SYSTEM FOR SURGICAL INSTRUMENT

[76] Inventor: Jaime Zacharias, Fundación Oftalmoldgica Los Andes, Las Hualtatas 5951, Santiago, Chile

[21] Appl. No.: 654,586

[22] Filed: May 29, 1996

Related U.S. Application Data

[63] Continuation-in-part of Ser. No. 321,116, Oct. 11, 1994, abandoned.

[51] Int. Cl.$^6$ ............................................... A61B 17/36
[52] U.S. Cl. ............................... 606/1; 606/51; 606/205
[58] Field of Search .......................... 606/1, 10–12, 606/41, 42, 45–52, 131, 133, 205–206; 81/300

[56] References Cited

U.S. PATENT DOCUMENTS

| | | |
|---|---|---|
| 3,785,381 | 1/1974 | Lower et al. .................... 606/122 |
| 4,573,466 | 3/1986 | Simada et al. ................... 606/11 |
| 5,360,426 | 11/1994 | Muller et al. ..................... 606/10 |
| 5,361,583 | 11/1994 | Huitema .......................... 606/205 |
| 5,494,485 | 2/1996 | Gabion et al. .................... 606/133 |
| 5,609,607 | 3/1997 | Hechtenberg et al. ............. 606/205 |

Primary Examiner—Michael Peffley

[57] ABSTRACT

A surgical instrument controller and actuating system that allows precise hand operated control of a powered instrument based on the detection of variations on the gripping force by means of pressure sensors located on the instrument handle. The grip pressure signal is processed by an electronic actuator controller which in turn drives an actuator system. The actuator system produces an actuation force that is proportional to the gripping force change detected at the instrument handle. The actuation force is transmitted to the active members of the instrument allowing precision proportional activation of surgical instruments such as micro forceps and micro scissors. The system allows an operator to precisely regulate the action of a surgical instrument by variation of the griping force applied over the handle of the instrument.

12 Claims, 6 Drawing Sheets

CONTROLLER AND ACTUATING SYSTEM FOR SURGICAL INSTRUMENT

This application is a continuation in part of earlier filed application Ser. No. 08/321,116 filed Oct. 11, 1994, now abandoned.

TECHNICAL FIELD

This invention relates to surgical instruments mainly used in micro-surgical procedures that require precise hand operated control.

BACKGROUND ART

Current intraocular micro surgical techniques require the use of very small sized instruments such as micro forceps, micro scissors and others which must be manipulated inside the eye with extreme precision under microscopic vision. The size of the active portion of such instruments usually varies between 0.3 and 3.0 mm. The actuating mechanism of these instruments is normally found in the handle of the same and composed of small levers or sliders that must be operated with the fingers of the same hand which holds the instrument. Instruments presently used for intraocular surgery require a displacement of the actuating levers of about 8 millimetres and demand a force of approximately 0.1 Kg to initiate displacement, the required force increases to about 0.2 Kg at the end of the stroke. The movement of the fingers which is necessary to operate the actuating mechanism of the instrument produces undesired vibrations that are transmitted to the active tip of the instrument. These vibrations can dramatically reduce precision and the time needed to obtain the desired surgical objectives. Such problem is of special interest in some intraocular surgical procedures where millimetric accuracy is a must.

Another limiting factor with existing finger activated instruments is that the actuating levers located at the handle are specific with respect to orientation, i.e. the instrument must be held in a particular position to allow the fingers to have adequate control of the actuating levers. Considering that microforceps and microscissors function in a specific orientation, the operator is forced to use the other hand in operating an orientation wheel for adjustment of the direction of the active tip of the instrument once the handle of the instrument has been properly held; normally the orientation wheel is located in between the handle portion of the instrument and the active tip portion of the same. This operation has to be repeated several times thus distracting the opposite hand from performing other required tasks, i.e. holding the endo-illumination probe; this results in increased surgical time.

In order to avoid the aforementioned inconvenience, instruments which are operated by foot actuated controls have been developed. The control of the instrument operation has been changed from direct hand actuation to foot pedal powered surgical instruments. This approach presents an improvement to the art and solves the problems posed by the transmission of the movements of the fingers to the active tip of the instrument. The instrument tip orientation problem is solved as well with this approach since the handle portion while being free of actuating levers, can be easily rotated single handed to position the active tip in the desired direction. This solution however is not entirely satisfactory since it adds one more pedal control device to those which are commonly used. The surgeon is normally using both feet to operate pedal controls of other instruments i.e. operating microscope, vitrectomy equipment, laser photo coagulators, coagulators and others.

OBJECTS OF THE INVENTION

It is therefore an object of the present invention to provide a surgical instrument controller and actuating system that will allow the use of the gripping hand for a precise control of surgical instruments, wherein said system avoids the transmission of the movements imparted by the fingers while operating the actuating means of the instrument to the active tip of the same.

It is another object of the present invention to provide a surgical instrument controller and actuating system which allows the handle to be not specific regarding radial orientation and thus allow single handed rotation to properly align the active tip according to the surgical objective.

DISCLOSURE OF THE INVENTION

The present invention provides a surgical instrument controller and actuating system wherein the handle the instrument is equipped with at least one pressure sensing element for the detection of the gripping pressure exerted by the operator, wherein an electric signal produced by the pressure sensing elements is transmitted through adequate conductors to an electronic controller which is designed to activate an actuator system in proportion to the pressure detected at the grip portion of the handle of the instrument. The actuator system transmits a proportional actuation force by adequate means to the actuated elements conforming the active portion of the instrument. The operator thus adjusts the action of the instrument by regulating the pressure of the fingers on a pressure-sensitive portion in the handle of the instrument. Unwanted displacement and vibration of the tip of the instrument normally occurring in existing manually actuated instruments is dramatically reduced.

BRIEF DESCRIPTION OF THE DRAWINGS

While the specification concludes with claims that particularly point out and distinctly claim the subject matter regarded as forming the present invention, it is believed that it will be better understood from the following detailed description, by the way of example only, with reference to the drawings in which:

Figure 1:
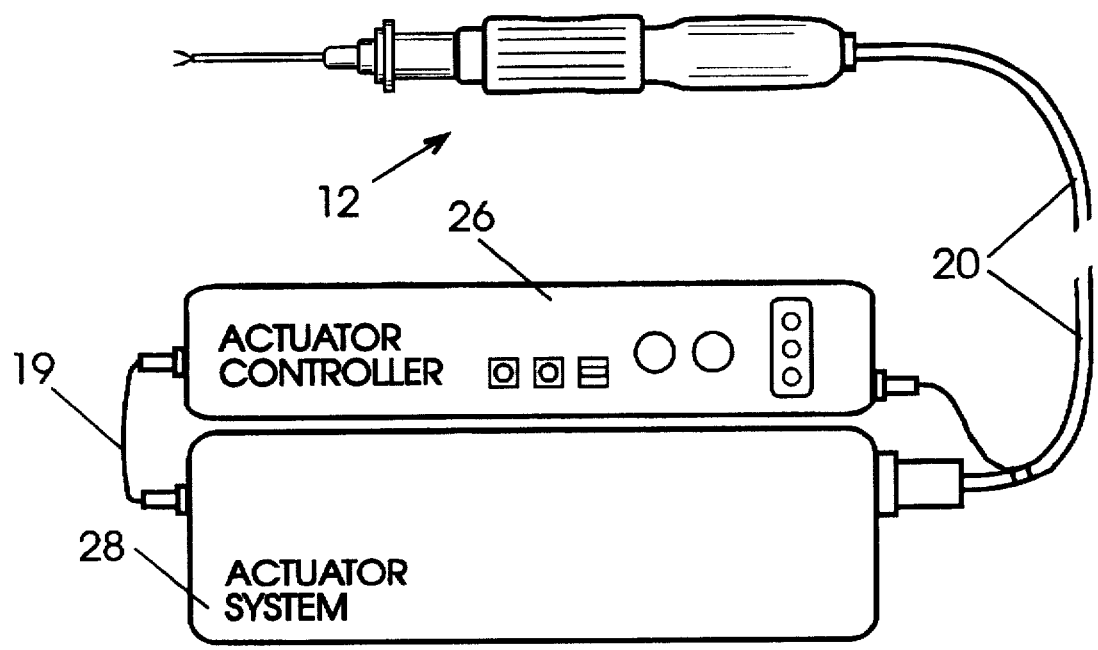
FIG. 1 shows an overall schematic view of the main composing elements of this surgical instrument and their interconnections.

| Reference Numerals in Drawings | | | |
|---|---|---|---|
| 12 | hand-piece | 56 | read only memory |
| 14 | gripping area | 58 | reset push-button |
| 15 | housing | 60 | control panel |
| 16 | active portion | 62 | operation push-button |
| 17 | external hollow cylinder | 64 | Forward/Reverse Positioning switch |
| 18 | opposing actuated members | | |
| 19 | bi-directional electric connector | 68 | Set Open Position LED |
| 20 | flexible conductor | 70 | Set Closed Position LED |
| 21 | isolated power supply | 72 | Ready to Operate LED |
| 22 | power supply electric conductors | 74 | stepping motor driving circuit |
| 23 | signal electric conductor | | |
| 24 | hydraulic tubing | 76 | stepping motor |
| 26 | electronic actuator controller | 78 | shaft |
| 28 | actuator system | 80 | gear |
| 30 | rod | 82 | toothed rod |
| 31 | fluid filled chamber | 83 | miniature disc load cell |
| 32 | miniature pressure transducer | 84 | linear actuator rod |
| 33 | connecting tubing | 85 | load cell conditioning circuit |
| 34 | strain gauge leads | | |
| 35 | conditioning amplifier | 86 | optical sensor |
| 36 | strain gauges | 87 | flexible electric conductors |
| 37 | grip pressure sensing circuit | 88 | hydraulic compression bellows |
| 38 | elastic cover | | |
| 40 | expansion bellows | 90 | mechanical detachable connector |
| 43 | cylinder | | |
| 44 | compression spring | | |
| 46 | preamplifier circuit | | |
| 48 | signal gain potentiometer | | |
| 50 | bias adjustment potentiometer | | |
| 51 | low-pass filter | | |
| 52a | analog-to-digital converter (a) | | |
| 52b | analog-to-digital converter (b) | | |
| 54 | microprocessor | | |

DETAILED DESCRIPTION OF THE INVENTION

FIG. 1 shows an overall view of the surgical system with its main components and their interconnections. A surgical instrument hand piece 12 is connected through a flexible conductor 20 to an electronic actuator controller 26 and to an actuator system 28. Controller 26 and actuator system 28 are interconnected through a bi-directional electric connector 19.

Figure 2:
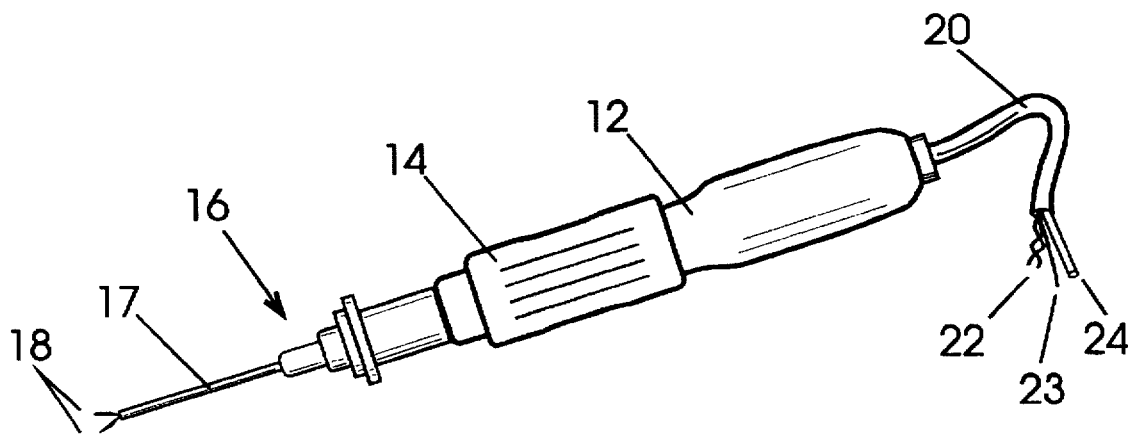
FIG. 2 is an schematic overall view of the hand held portion of the surgical instrument.

FIG. 2 shows a detailed view of the surgical instrument shown in FIG. 1 composed of a hand-piece 12 having a gripping area 14 at the anterior portion of hand-piece 12. Gripping area 14 is positioned to approximately match the location of the gripping fingers of an operator. Hand-piece 12 is designed with radial symmetry to allow single handed rotation by the operator. An active portion 16 extends from one end of hand-piece 12. Active portion 16 carries the elements that determine the function of instrument hand piece 12, generally consisting in a pair of opposing actuated members 18 configuring micro forceps or micro scissors, merging from the tip of an external cylinder 17. The opposite end of hand-piece 12 receives flexible shield 20 enclosing a group of electrical conductors 22 and 23 and a flexible hydraulic tubing 24.

Figure 3A:
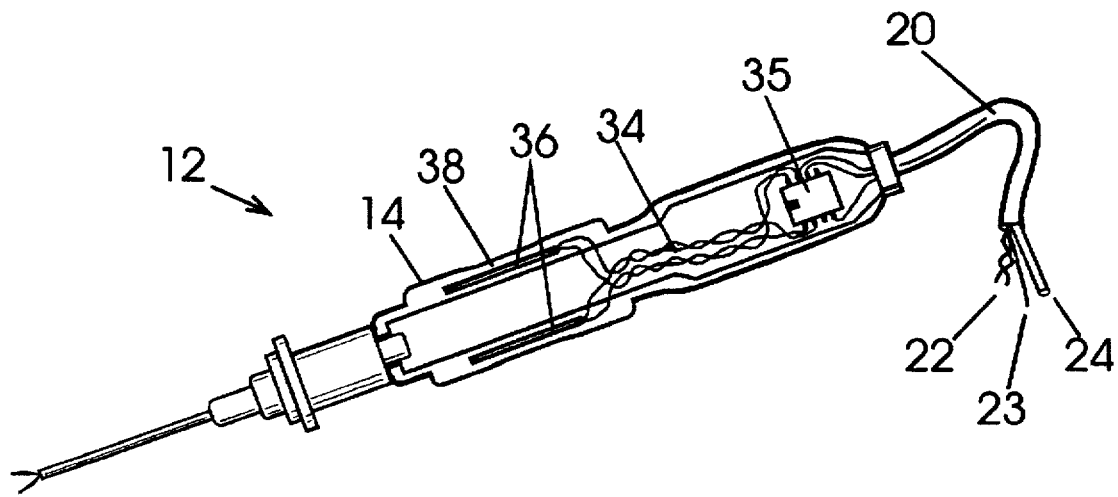
FIG. 3(a) is an schematic longitudinal cross sectional view of the instrument hand piece illustrated in FIG. 2 showing grip pressure sensing elements composed of strain gages used to operate the instrument.

FIG. 3(a) is an schematic longitudinal cross sectional view of hand piece 12 illustrated in FIG. 2 showing the gripping force detection elements. These consist in a set of semiconductor strain gauges 36 properly arranged beneath gripping area 14 and covered by an elastic cover 38. Leads 34 of strain gauges 36 connect to the input terminals of a miniature conditioning amplifier 35 configuring a grip pressure sensing circuit 37 enclosed within hand piece 12, further described in FIG. 4. Pressure sensing circuit 37 is powered through conductors 22 and its output signal is connected to conductor 23. Electrical conductors 22 and 23 connect at the opposite end of shield 20 to electronic controller 26 described in FIG. 6.

Figure 3B:
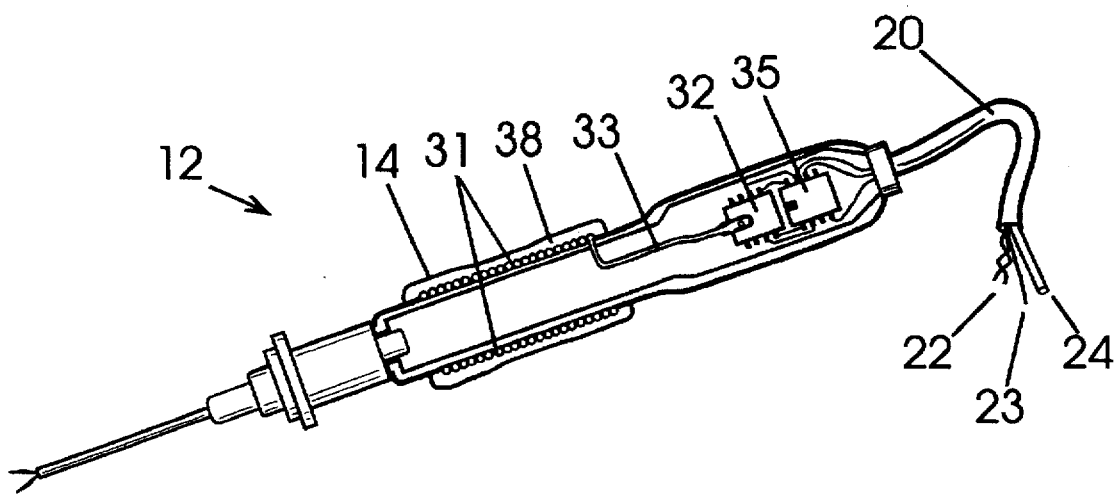
FIG. 3(b) is an schematic longitudinal cross sectional view of the instrument hand piece illustrated in FIG. 2 showing an alternative embodiment of grip pressure detector based on a fluid chamber located at the grip portion of the hand piece connected to a miniature pressure transducer located inside the instrument hand piece.

FIG. 3(b) is an schematic longitudinal cross sectional view of hand piece 12 illustrated in FIG. 2 showing an alternative embodiment of gripping force detection system. This consists in a fluid filled circular chamber 31 located beneath gripping area 14 and covered by elastic cover 38. Fluid chamber 31 is manufactured using a thin silicone rubber tubing coiled under gripping area 14 with one end closed and the other end connected to the input of a pressure transducer 32, whose output signal if fed through leads 34 to the input terminals of miniature conditioning amplifier 35 configuring grip pressure sensing circuit 37 enclosed within hand piece 12.

Figure 4:
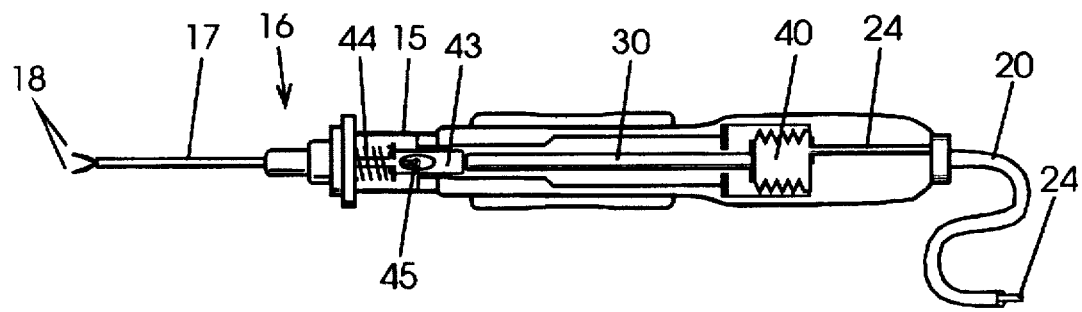
FIG. 4 is an schematic longitudinal cross sectional view of the instrument illustrated in FIG. 2 showing the enclosed actuating elements.

FIG. 4 is an schematic longitudinal cross sectional view of instrument hand piece 12 illustrated in FIG. 2 showing the actuator elements enclosed within hand piece 12. Hydraulic tubing 24 connects to an hydraulic expansion bellows 40 axially oriented inside hand-piece 12. Expansion bellows 40 is in axial contact with a rod 30. Rod 30 contacts the moving part of the active portion 16 composed of cylinder 43 narrowed distally to conform external cylinder 17. A spring 44 forces the closed end of cylinder 43 against rod cylinder 30. Opposing members 18 extend outwards from the tip of cylinder 17 and are fixed at the proximal end by an anchoring screw 45 to the internal aspect of a housing 15. Axial distal displacement of cylinder 17 forces the approximation of opposing members 18 preserving their relative distance to hand-piece 12. Hydraulic tubing 24 connects at the opposite end of conductor 20 to hydraulic actuator system 28 shown in FIG. 5.

Figure 5:
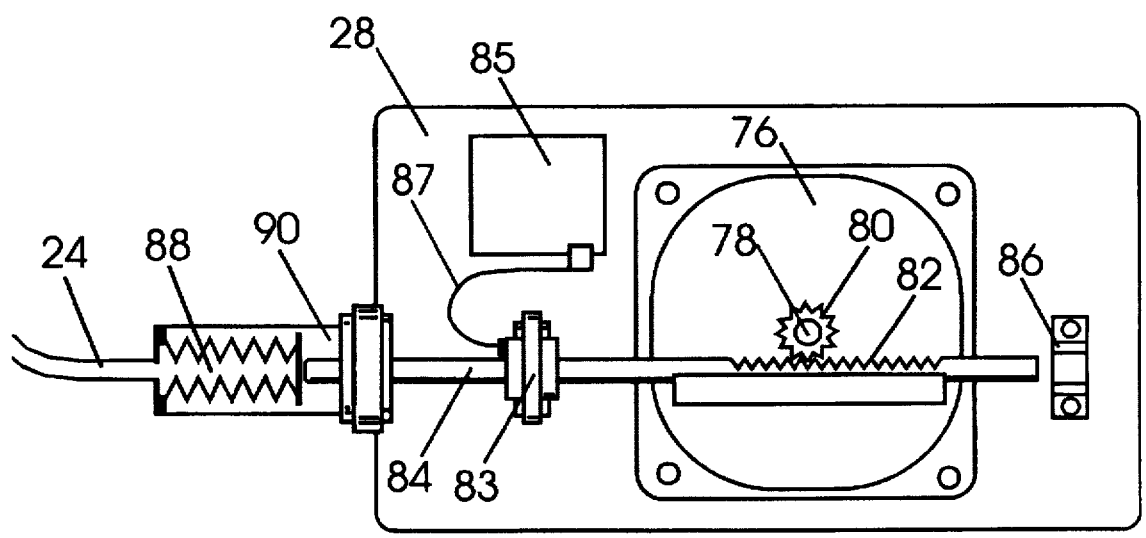
FIG. 5 is an schematic view of the actuator system that remotely drives the hand held portion of the surgical instrument.

FIG. 5 illustrates actuator system 28 where a shaft 78 of a stepping motor 76 (Type 103-770-0113 Sanyo Denki Co. or similar) has an axially mounted pinion gear 80. The teeth of gear 80 engage with a toothed rod 82 that couples to a linear actuator rod 84 having an interposed load cell 83 (ELF-13, Entran Devices, USA. or similar). An optical sensor 86 is properly located in the path of rod 82 providing a digital signal that indicates the relative position of rod 82 with regard to optical sensor 86. The digital signal changes logical status when the optical path is interrupted by axial displacement of rod 82. The electrical signals of load cell 83 connect through a sheet of flexible conductors 87 to a conditioning circuit 85. The digital output of optical position sensor 86 and the analog output of load cell conditioning circuit 85 are connected to inputs of actuator controller 26 through connector 19. Linear actuator rod 84 is arranged to axially couple with an hydraulic compression bellows 88. As seen in the sectional view, compression bellows 88 is enclosed within a detachable connector 90 and connects to hydraulic tubing 24. Compression bellows 88, hydraulic tubing 24 and expansion bellows 40 conform a sealed hydraulic unit detachable from actuator system 28 and designed to transmit actuation energy to instrument hand piece 12 and withstand sterilisation conditions.

Figure 6:
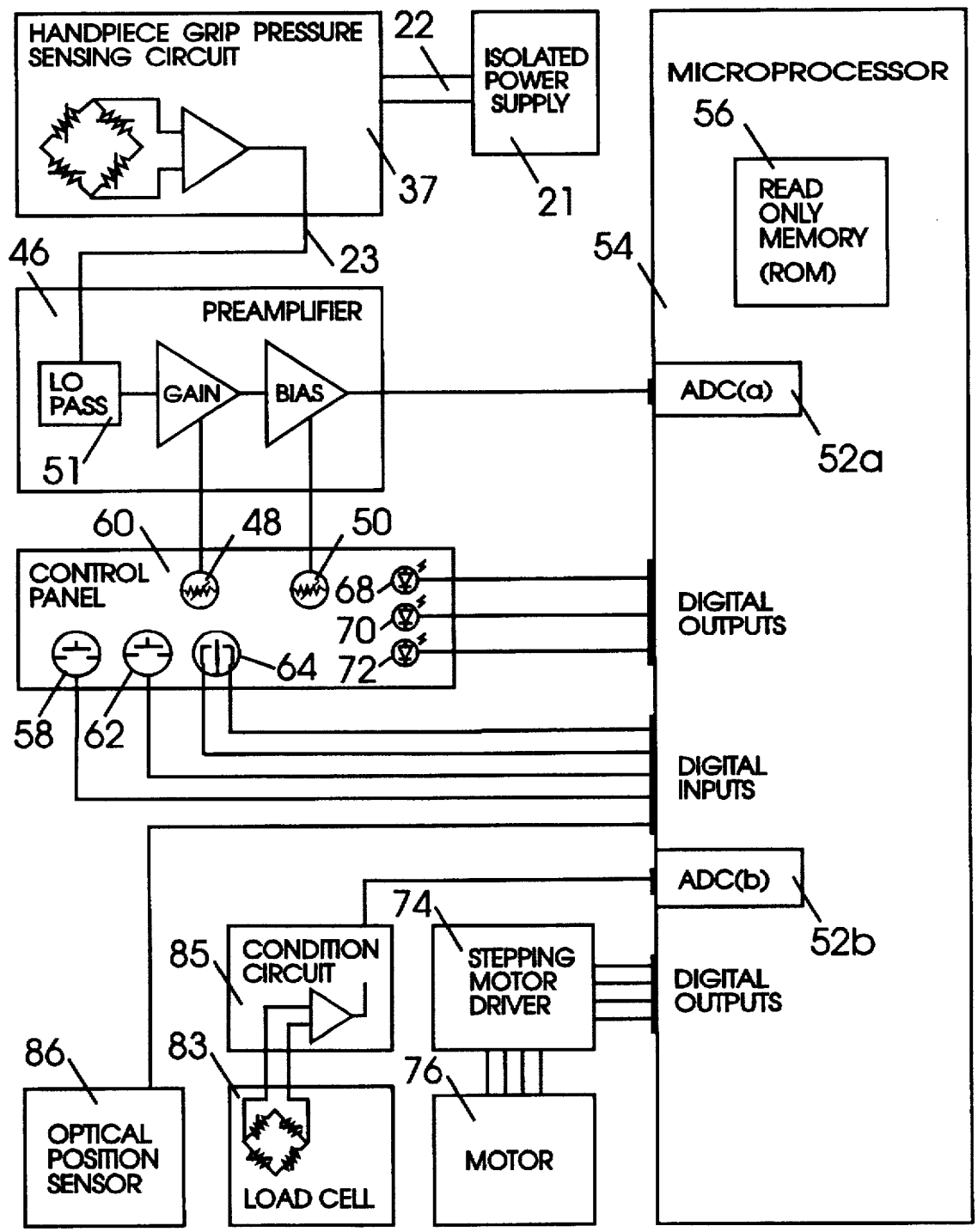
FIG. 6 is an schematic block diagram showing the electronic actuator controller and related elements involved in operation of the instrument.

As shown in FIG. 6, grip pressure sensing circuit 37 is connected to an isolated power supply 21 through conductors 22. The output signal of circuit 37 is fed trough conductor 23 to a preamplifier circuit 46 located inside electronic controller 26. Preamplifier circuit 46 provides a gain adjustment potentiometer 48 and a bias adjustment potentiometer 50 that can be regulated at a control panel 60.

A low-pass filter 51 is incorporated into preamplifier circuit 46. The output of preamplifier circuit 46 is connected to an analog-to-digital converter 52a that is integral part of a microprocessor 54 (Motorola 68705R3 or similar). Analog-to-digital converter 52a gives an 8 bit equivalent digital reading of the voltage applied at its input. Microprocessor 54 executes a computer program stored in a non-volatile read only memory 56. Control panel 60 also contains a reset push-button 58, an operation push-button 62 and a Forward/Reverse (ON)OFF(ON) positioning switch 64, all connected to digital inputs of microprocessor 54. Control panel 60 also contains a Set Open Position LED 68, a Set Closed Position LED 70 and a Ready to Operate LED 72 connected to selected digital outputs of microprocessor 54. Microprocessor 54 provides dedicated digital output lines which are connected to corresponding inputs of stepping motor driver circuit 74. Each output of stepping motor driving circuit 74 is connected to one of the phases of stepping motor 76 inside actuator system 28. Microprocessor 54 receives position and force feedback signals from actuator system 28. The signal from sensor 86 is connected to a determined digital input. The signal from load cell conditioning circuit 85 is connected to an integrated 8 bit analog-to-digital converter 52b.

OPERATION OF THE INVENTION

Figure 7A:
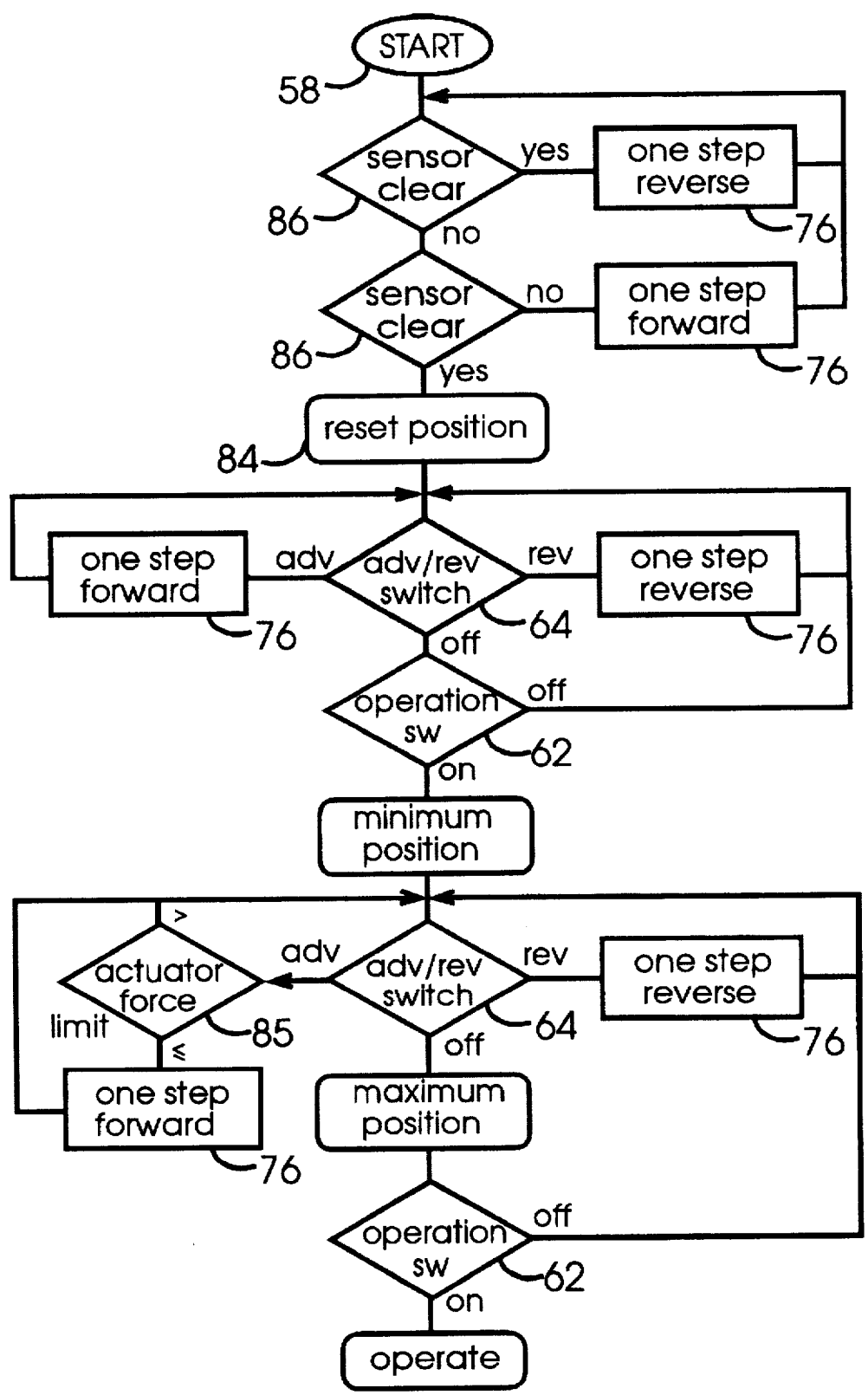
FIG. 7(a) is a flow chart of the basic logic used in the controller reset and calibration process.
Figure 7B:
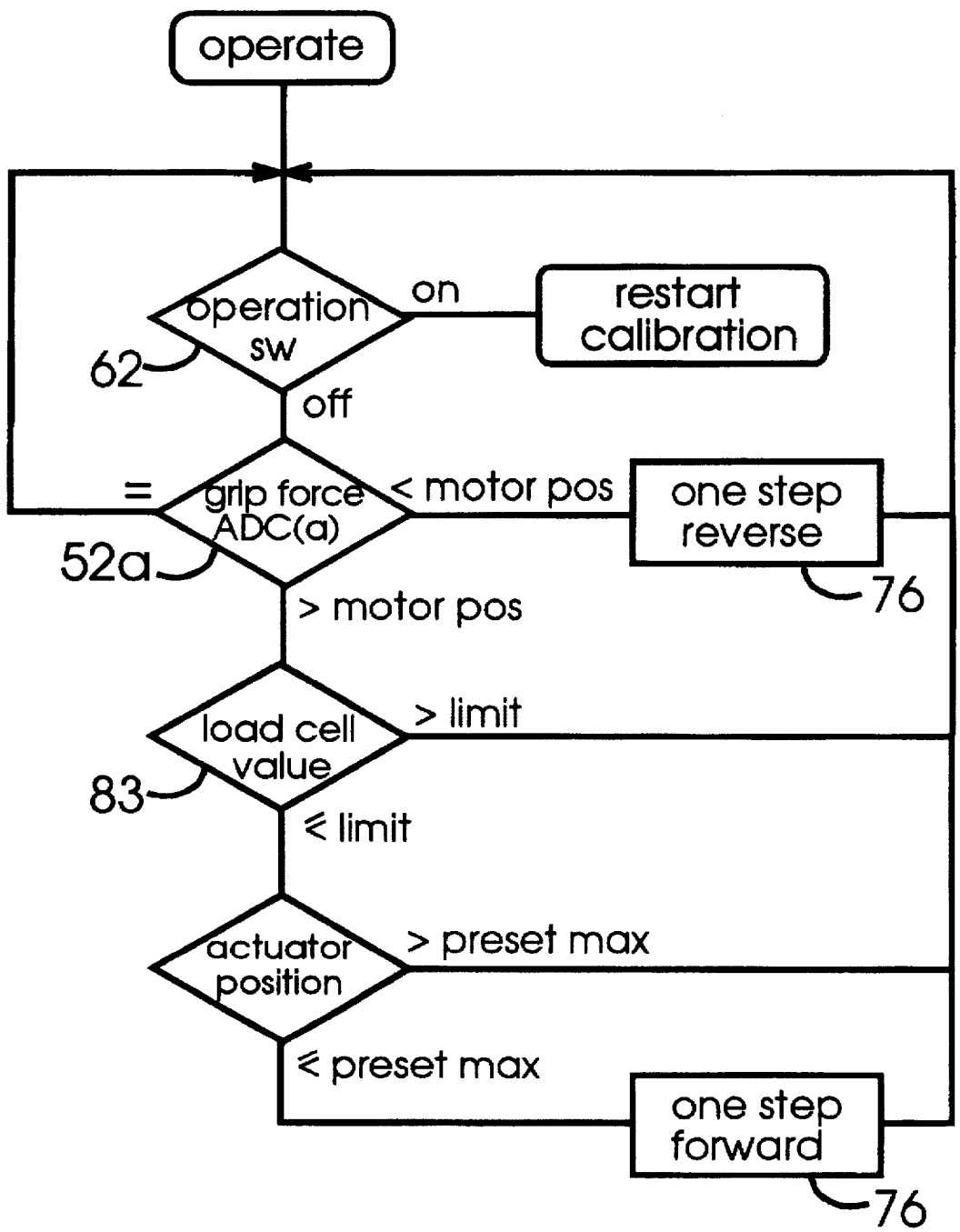
FIG. 7(b) is a flow chart of the basic logic used in the controller operation process.

The operation of this surgical instrument will be described by making reference to functional parts detailed in the preceding figures as well the flowcharts of FIGS. 7a and 7b.
Calibration:

The operation of the surgical instrument requires an initial set-up process that starts when the system is powered up or when reset push-button 58 is pressed. Under these conditions microprocessor 54 is instructed to start executing the program stored in read only memory 56. The first action consists in positioning toothed rod 82 and linear actuator 84 assembly at the reset position. This action is performed by reading the logical status of optical sensor 86 and providing the necessary control logic to stepping motor driving circuit 74. Stepping motor driving circuit 74 provides the power signals to operate stepping motor 76. Rotation of shaft 78 and gear 80 linearly displace engaged rod 82. The reset position is reached when rod 82 is positioned one unit step of rotation of stepping motor 76 ahead of the optical occlusion point of optical sensor 86. Once this process is completed, Set Open Position LED 68 in control panel 60 lights up instructing the operator to start the calibration process of the actuated members 18. By pulsing Forward/Reverse Positioning Switch 64 in the corresponding direction the operator instructs microprocessor 54 to slowly advance or reverse linear actuator 84. Linear actuator 84 axially interacts with hydraulic compression bellows 88 inside connector 90 applying or relieving an actuation force that is hydraulically transmitted through hydraulic tubing 24 to expansion bellows 40 inside hand-piece 12. Expansion bellows 40 axially expands or retracts according to the current hydraulic pressure axially transmitting actuation force to external cylinder 17 through the interposed elements shown in FIG. 4. Axial displacement of outer cylinder 17 forces approximation of opposing actuated members 18 at the tip of the active portion 16 of instrument hand piece 12. Compression spring 44 retracts outer cylinder 17 when axial pressure is relieved producing the separation of opposing actuated members 18 based on the intrinsic flexibility of their constituting material. At this step the operator can regulate the desired open position of actuated members 18. Once this task is completed the operator presses operation push-button 62 to instruct microprocessor 54 to go to the next step of calibration. At this stage a relative value of zero is assigned to the position counter of stepping motor 76 in microprocessor 54 random access memory. Set Closed Position LED 70 lights up instructing the operator to proceed now with the adjustment of the closed position desired for actuated members 18. The process is similarly performed using Forward/Reverse Positioning Switch 64 until a satisfactory adjustment is reached. Load cell 83 permanently informs microprocessor 54 of the force present within the actuator system so it can be stopped from increasing force when a pre-set limit is reached providing a mechanism to warn the operator and protect sensible elements from overloading. The operator presses again operation push-button 62 to instruct microprocessor 54 that the calibration and adjustment process has ended. In this way the operator determines the desired span of operation of the actuated members 18 of micro instrument hand piece 12. Once the system is calibrated, Ready to Operate LED 72 lights up indicating that the system is set for operation. Operation push-button 62 can be pressed at any time to repeat the calibration process from the beginning.
Operation:

The operation process of the surgical instrument involves the detection of the gripping force applied by the operator over gripping area 14 located on hand-piece 12. The gripping force is transmitted though elastic cover 38 causing proportional deformation of strain gauges 36. Strain gages 36 and conditioning amplifier 35 conform a temperature compensated pressure sensing circuit 37 producing an output voltage that varies in proportion to the gripping force applied. As an alternative embodiment we describe a grip pressure sensor based on compression of fluid filled chamber 31 connected to miniature pressure transducer 32 (such as NPP-301, Lucas Nova Sensor, Calif., USA) as the detection component of pressure sensing circuit 37. Fluid chamber 31 is filled with low viscosity silicone oil whose electric and physical properties are compatible with pressure transducer 32 operation. Pressure sensing circuit 37 is powered by an electrically isolated power supply 21 through electric conductors 22. The output signal is transmitted by conductor 23 to preamplifier circuit 46. Signal gain potentiometer 48 adjusts the sensitivity of operation. By regulating gain potentiometer 48 the user determines the gripping pressure variation that will actuate the full desired span of actuated members 18 of micro instrument hand piece 12. Bias adjustment potentiometer 50 sets the threshold gripping pressure that will initiate operation of actuated members 18 of micro instrument hand piece 12. By regulating bias adjustment potentiometer 50 the user determines the amount of gripping pressure allowed to hold and manipulate hand piece 12 without initiating instrument operation. Above this threshold grip pressure, actuated members 18 will enter into operation in proportion to grip pressure change as determined by the gain setting selected with gain potentiometer 48. Low-pass filter 51 included in preamplifier circuit 46 reduces high frequency oscillations that degrade system performance.

The computer program stored in read only memory 56 instructs microprocessor 54 to compare the current position counter value of stepping motor 76 to the digital equivalent of the filtered, preamplified and biased grip force signal provided to analog-to-digital converter 52 by preamplifier circuit 46. If the grip force value is higher than the position value of the stepping motor 76 then a single unit step of rotation of stepping motor 76 is instructed in direction to increase the pressure applied by linear actuator 84 to compression bellows 88. If the grip force value is lower than the position counter value of stepping motor 76 then a single unit step of rotation of stepping motor 76 is instructed in direction to decrease the pressure applied by linear actuator 84 to compression bellows 88. If the grip force value coincides with the position counter value of stepping motor 76 no action is taken. According to this logic, actuated members 18 open and close following variations in the gripping force applied. Stepping motor 76 minimum and maximum position limits are determined by the initial calibration process and are stored in microprocessor 54 random access memory allowing the displacement of actuated members 18 only between the pre-set span. Load cell 83 output is permanently monitored by microprocessor 54 keeping track of the current axial force present in linear actuator 84. This force measurement is used to limit by software the maximum allowable actuation force, to avoid system overloads that could produce malfunctioning or damage.

The software routine described conforms a loop adjusted to repeat at a rate that allows adequate driving of stepping motor 76 and related elements of actuator system 28 providing the best response characteristics of actuated members 18. FIGS. 7a and 7b are flow charts that illustrate the logic used in microprocessor 54 operation.

CONCLUSIONS, RAMIFICATIONS AND SCOPE

Accordingly, the reader will understand from the previous description that this surgical instrument allows precise hand operation with a minimum of unwanted vibration and displacement at the active portion, due to the use of a grip pressure sensing device that detects variations in the gripping force whose output is used to electronically drive an actuator, producing a proportional adjustable effect on the actuated members of the instrument. A significant advantage of this system is the enhanced precision obtained by relieving the gripping hand that holds the instrument from displacing levers that directly apply the actuation force that operates the instrument. By placing the sensor elements in the grip portion of the instrument, the activation mechanism is kept in relation to the hand that holds the instrument, making the operation of the instrument more natural and avoiding the inconvenience of introducing a foot pedal for this purpose.

Having thus described the invention, it will be apparent to those skilled in the art that various modifications can be made without departing from the scope of the invention. The description contains many specificities and these should not be construed as limiting the scope of the invention but as merely providing illustration of a presently preferred embodiment.

For example, the pressure sensing circuit can integrate a miniature analog-to-digital converter within the handle of the instrument, transmitting a digital instead of analog signal to the actuator controller, in order to improve noise immunity. The operation gain and threshold adjustments can be performed at a microprocessor level. The electronic controller system can include an auto-zeroing circuit to compensate for thermal and component related baseline drifts originating at the analog portions of the detector circuit. Software algorithms can be included in the microprocessor program to make it respond to particular temporal patterns of gripping force change with specific actions, for example, to fully close the actuated elements of the instrument for introduction or withdrawal from the surgical field after a rapid sequence of two strong grips. The grip force-actuator response curve can be modified by software to depart from linear when it shows to enhance system operation. The actuator system can replace hydraulic transmission of the actuation force to the instrument handle by the use of alternative energy transmission means such as electric, pneumatic, mechanic, or others. The actuator system can be included within the hand-piece of the instrument in the way of miniature stepping motors, servo motors, linear magnetic actuators, or others. The actuated members of the surgical instrument can vary in nature depending on the specific function to be performed, extending beyond micro-forceps and micro-scissors, but also considering vitrectomy probes, electric coagulators and scalpels, aspirators, irrigators, and other surgical instruments suitable to be proportionally actuated by means of an electronic controller system regulated by the gripping force applied by the operator over a pressure sensing area on the hand piece of the instrument.

Thus, the scope of this invention should be determined by the appended claims and their legal equivalents, rather than by the examples given.

I claim:

1. A surgical system wich allows precise proportional hand operated control by detection of grip force variations of a gripping hand at an instrument handpiece comprising:

(a) a surgical instrument hand piece;

(b) actuated members extending from said surgical instrument hand piece;

(c) a grip portion being part of said surgical instrument hand piece;

(d) grip pressure sensing means arranged within said surgical instrument hand piece to produce a proportional electric signal corresponding to the grip force detected at said grip portion, (e) an electronic controller that processes said proportional electric signal and generates an actuator driving signal;

(f) an actuator system that receives said actuator driving signal producing a proportional actuation force;

(g) energy conducting means for transmitting said actuation force from said actuator system to said actuated members of said surgical instrument hand piece;

(h) conductor means for transmitting electric signals between said grip pressure sensing means located within said surgical instrument hand piece and said electronic controller.

2. The system of claim 1 wherein said actuated members are connected to a micro forceps to control actuation of said forceps.

3. The system of claim 1 wherein said actuated members are connected to a micro scissors to control actuation of said scissors.

4. The system of claim 1 wherein said grip pressure sensing means are located in relation to said grip portion to detect the gripping force of at least one of the fingers of an operator.

5. The system of claim 1 wherein said grip pressure sensing means are composed by strain gauges contained within said hand piece.

6. The system of claim 1 wherein said grip pressure sensing means are composed by a sealed fluid chamber connected to a miniature pressure transducer enclosed within said hand piece.

7. The system of claim 1 wherein said grip pressure sensing means are properly arranged to allow accurate grip force detection regardless of hand piece orientation.

8. The system of claim 1 wherein the electronic controller operates under microprocessor control providing a control panel.

9. The electronic actuator controller of claim 8 wherein said control panel includes means for adjusting the sensitivity and threshold of operation of said powered surgical instrument.

10. The system of claim 1 wherein said electronic controller includes electronic control means for activating said actuator system.

11. The system of claim 1 wherein said actuator system is composed by a linear actuator powered by a stepping motor including position and force sensing means that provide feedback to said electronic controller to monitor the action of said actuator system.

12. The system of claim 1 wherein said actuated members are energised by said energy conducting means in proportion to the actuation force transmitted from said actuator system.

* * * * *